(12) United States Patent
Sambandan et al.

(10) Patent No.: US 7,132,117 B2
(45) Date of Patent: Nov. 7, 2006

(54) **BIOACTIVE FRACTION OF *EURYCOMA LONGIFOLIA***

(75) Inventors: T.G. Sambandan, Cambridge, MA (US); ChoKyun Rha, Cambridge, MA (US); Azizol Abdul Kadir, Kuala Lumpur (MY); Norhaniza Aminudim, Kuala Lumpur (MY); Joharl Mohammed Saad, Kuala Lumpur (MY)

(73) Assignees: Government of Malaysia, Kuala Lumpur (MY); Massachusetts Institute of Technology, Cambridge, MA (US)

( * ) Notice: Subject to any disclaimer, the term of this patent is extended or adjusted under 35 U.S.C. 154(b) by 174 days.

(21) Appl. No.: 10/362,697

(22) PCT Filed: Feb. 14, 2001

(86) PCT No.: PCT/US01/40101

§ 371 (c)(1),
(2), (4) Date: Dec. 12, 2003

(87) PCT Pub. No.: WO02/17946

PCT Pub. Date: Mar. 7, 2002

(65) Prior Publication Data

US 2004/0087493 A1    May 6, 2004

(30) Foreign Application Priority Data

Aug. 29, 2000 (MY) .............. PI 2000 3988

(51) Int. Cl.
*A61K 35/78* (2006.01)
*A61K 38/16* (2006.01)
*A61K 38/00* (2006.01)

(52) U.S. Cl. .............. 424/724; 514/8; 514/12
(58) Field of Classification Search ........ 424/725; 514/8, 12
See application file for complete search history.

(56) References Cited

U.S. PATENT DOCUMENTS

| | | | | | |
|---|---|---|---|---|---|
| 4,357,934 | A | * | 11/1982 | Fahim | 600/33 |
| 4,731,459 | A | * | 3/1988 | Tada et al. | 549/275 |
| 6,905,714 | B1 | * | 6/2005 | Ong et al. | 424/769 |
| 2001/0046524 | A1 | * | 11/2001 | Ong et al. | 424/769 |
| 2004/0253326 | A1 | * | 12/2004 | Mesko | 424/725 |

OTHER PUBLICATIONS

Ang et al. Exp. Anim. Jan. 2000. vol. 49, No. 1, pp. 35-38.*
Ang et al. Exp. Anim. 1997. vol. 46, No. 4, pp. 287-290.*
Ang et al. Jpn. J. Pharmacol. 1997. vol. 79, pp. 497-500.*
Ang et al. Pharm. Biol. 1998, vol. 36, No. 2, pp. 144-146.*
Database Biosis Online!, Biosciences Information Service, Philadelphia, PA, Jan. 2000; Ang Hooi Hoon, et al., "Effects of *Eurycoma longifolia* Jack (Tongkat Ali) on the initiation of sexual performance of inexperienced castrated male rates."
Database Biosis Online!, Biosciences Information Service, Philadelphia, PA, Apr. 1997, Ang Hooi Hoon, et al., "Enhancement of sexual motivation in sexually naïve male mice by *Eurycoma longifolia*."

* cited by examiner

*Primary Examiner*—Christopher R. Tate
(74) *Attorney, Agent, or Firm*—Wolf Greenfield & Sacks, PC

(57) ABSTRACT

The invention provides new uses and products for treatment of sexual dysfunction and male infertility. The products include bioactive components of extracts from roots of the plant *Eurycoma longifolia* mixed in preparations for topical application and administation.

16 Claims, 3 Drawing Sheets

Figure 1 – Isolation of Bioactive Fraction of *Eurycoma longifolia*

Characterization & Identification
of bioactive fraction - FDAE and F3AE

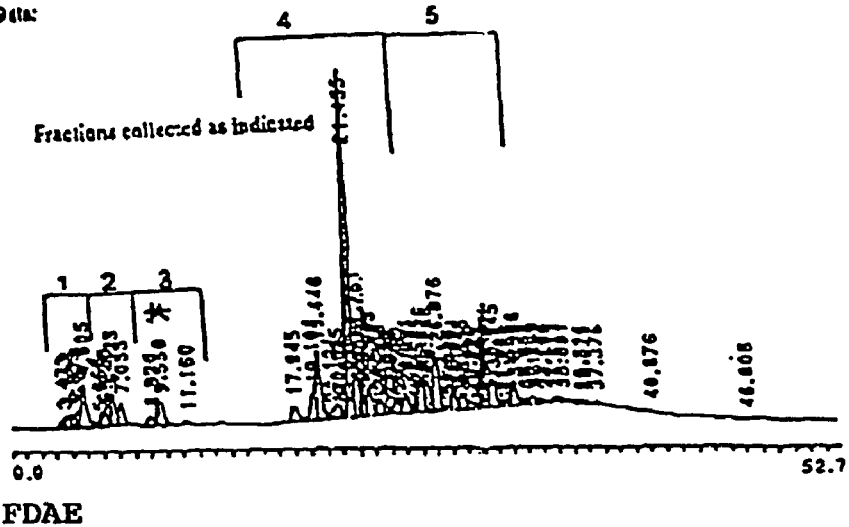
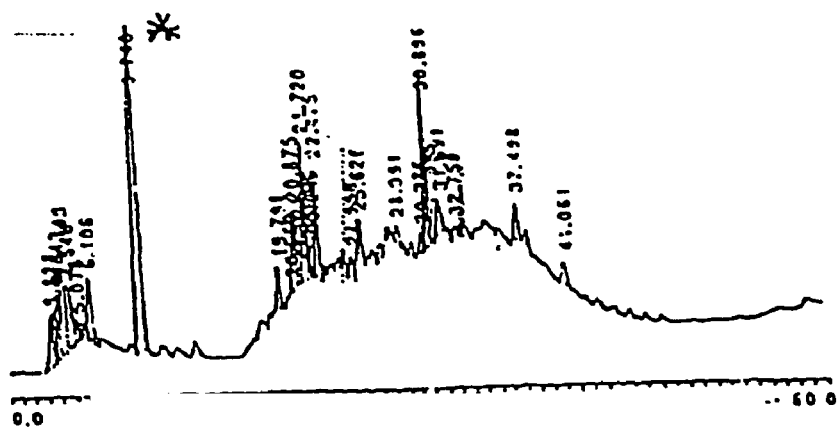
Figure 3 — Chromatogram of the Eurycoma Longifolia reverse-phase HPLC purification runs for FDAE (top trace) and F3AE (Lower trace)

BIOACTIVE FRACTION OF *EURYCOMA LONGIFOLIA*

RELATED APPLICATIONS

This application is a national stage filing under 35 U.S.C. §371 of PCT International application PCT/US01/40101, filed Feb. 14, 2001 which was published under PCT Article 21(2) in English.

FIELD OF THE INVENTION

The present invention relates generally to the field of bioactive natural products and, in particular, to composition derived from fractions of *Eurycoma longifolia*.

BACKGROUND OF THE INVENTION

Components of *Eurycoma longifolia*, also known in Malaysia as Tongkat Ali, have been used in traditional and folk medicine. Extracts of the plant are generally believed to be useful in the treatment of multiple disorders and syndromes such as: malaria, cancer, anxiety, ulcers, and male infertility and sexual dysfunction. In the past, much of the information on the medicinal value of the plant has been anecdotal. Well-controlled, repeatable extractions and bioactivity assays may clarify the function of components. For example, studies are underway to examine extracts of *Eurycoma longifolia* that have been shown to have cytotoxic effects. These extracts, which include quassinoids, encompass compounds such as eurycomalactone, eurycomanol, and eurycomanone, which have been examined for cytotoxic properties and potential use as anti-cancer, anti-malarial, and anti-ulcer agents.

Chromatographic processes for producing quassinoid extracts from *Eurycoma longifolia* were disclosed in Chan, et. al. (1998). This reference reports the potential usefulness of such quassinoid extracts in the treatment of cancer, ulcers, malaria, and fever.

In contrast to quassinoids, whose effects have been examined following stringent purification strategies, components of *Eurycoma longifolia* with possible aphrodisiac activity and potential as treatments for male infertility and sexual dysfunction have not been isolated. Crude butanol, methanol, water, and chloroform extracted-fractions of *Eurycoma longifolia* have been examined for behavioral effects in mammals. Mixtures of compounds separated with these basic methods have been administered to male mice and rats to assess effects on the animals sexual behaviors and performance.

Examination of the sexual effects of *Eurycoma longifolia* have focussed on the influence of the crude extracts on orientation activities of sexually experienced and naive male rats toward receptive females. Activities monitored in the treated rats include mounting, licking, and anogenital sniffing; and behaviors of the treated rats in relation to their environment were also assessed including analysis of activities such as movement, exploration, rearing, and climbing. In addition, rats were assessed for levels of genital and non-genital grooming. Analysis of these types of behavioral elements has served as the assay for investigating the anecdotal aphrodisiac properties of *Eurycoma longifolia* and administration of the crude extracts has been correlated with increased sexual performance of treated animals. Although use of behavioral assays indicate an effect on sexual physiology from crude *Eurycoma longifolia* extracts, the research has not utilized purification strategies yielding isolated components; therefore, the art has not identified the physical properties of the *Eurycoma longifolia* candidate aphrodisiac compounds or been able to assess the effects of compounds isolated from *Eurycoma longifolia* on infertility or sexual dysfunction at the cellular level.

SUMMARY OF THE INVENTION

It now has been discovered that particular purified components of *Eurycoma longifolia* aqueous extracts exhibit bioactivity of increasing testosterone synthesis and release and sperm activity and number. These purified components include peptides having a molecular weight of about 4300 daltons. Methods for treating male infertility and sexual dysfunction using the purified components are provided. Preparations including extracts of roots of the *Eurycoma longifolia* plant also are provided. The preparations may be formulated for application or administration by several routes.

According to one aspect of the invention, compositions including a fraction of an aqueous extract of *Eurycoma longifolia* are provided. The fraction comprises a peptide having a molecular weight of about 4300 daltons. In certain embodiments, the fraction has an activity selected from the group consisting of increasing testosterone synthesis, increasing testosterone release from cells, increasing sperm count, and increasing sperm motility. In some preferred embodiments, the peptide is a glycopeptide. In other preferred embodiments, the peptide has about 30–39 amino acids; preferably the peptide has about 36 amino acids.

According to another aspect of the invention, methods for isolating a bioactive component from an aqueous extract of *Eurycoma longifolia* are provided. The methods include preparing an aqueous extract of *Eurycoma longifolia*, and isolating the bioactive component from the fraction. The bioactive component is isolated by a chromatographic method, preferably one selected from the group consisting of reverse-phase high performance liquid chromatography (HPLC) and size-exclusion chromatography. The bioactive component comprises a peptide having a molecular weight of about 4300 daltons. In certain preferred embodiments, the reverse-phase HPLC is performed using a chromatographic medium selected from the group consisting of C4 and C18. In other embodiments, the methods further include fractionating the aqueous extract using at least one size-exclusion chromatography medium selected from the group consisting of Bio-Gel P-2 and Bio-Gel P-4 prior to separation by chromatography by reversed phase HPLC. In other preferred embodiments, the bioactivity is selected from the group consisting of increasing testosterone synthesis, increasing testosterone release from cells, increasing sperm count and increasing sperm motility.

According to still another aspect of the invention, bioactive components of *Eurycoma longifolia* prepared by the foregoing methods are provided.

According to yet another aspect of the invention, there is provided a composition comprising an aqueous extract of *Eurycoma longifolia* for use in the treatment of sexual dysfunction or male infertility. The use includes administering to a subject in need of such treatment an amount of a composition comprising a fraction an aqueous extract of *Eurycoma longifolia*. The fraction includes a peptide having a molecular weight of about 4300 daltons. The amount administered is effective to increase an activity selected from the group consisting of increasing testosterone synthesis, increasing testosterone release from cells, increasing sperm count and increasing sperm motility. According to further aspects of the invention, use of the composition comprising an aqueous extract of *Eurycoma longifolia* for increasing testosterone synthesis, increasing testosterone release from testis cells, increasing sperm count and/or increasing sperm motility are provided. The use includes administering to a subject in need of such treatment an amount of the foregoing *Eurycoma longifolia* compositions effective to increase testosterone synthesis, testosterone release from testis cells, sperm count and sperm motility, respectively.

According to still another aspect of the invention, pharmaceutical compositions are provided. The compositions include an effective amount of the foregoing compositions along with a pharmaceutically acceptable carrier.

These and other aspects of the invention will be described in greater detail below.

BRIEF DESCRIPTION OF THE DRAWINGS

FIG. 3 shows a chromatogram of the *Eurycoma longifolia* reverse-phase HPLC purification runs for FDAE (top trace) and F3AE (lower trace). Numbers and divisions across bottom of traces indicate time of elution in minutes. The asterisks (*) indicate bioactive fraction or peak.

DETAILED DESCRIPTION OF THE INVENTION

Figure 1:
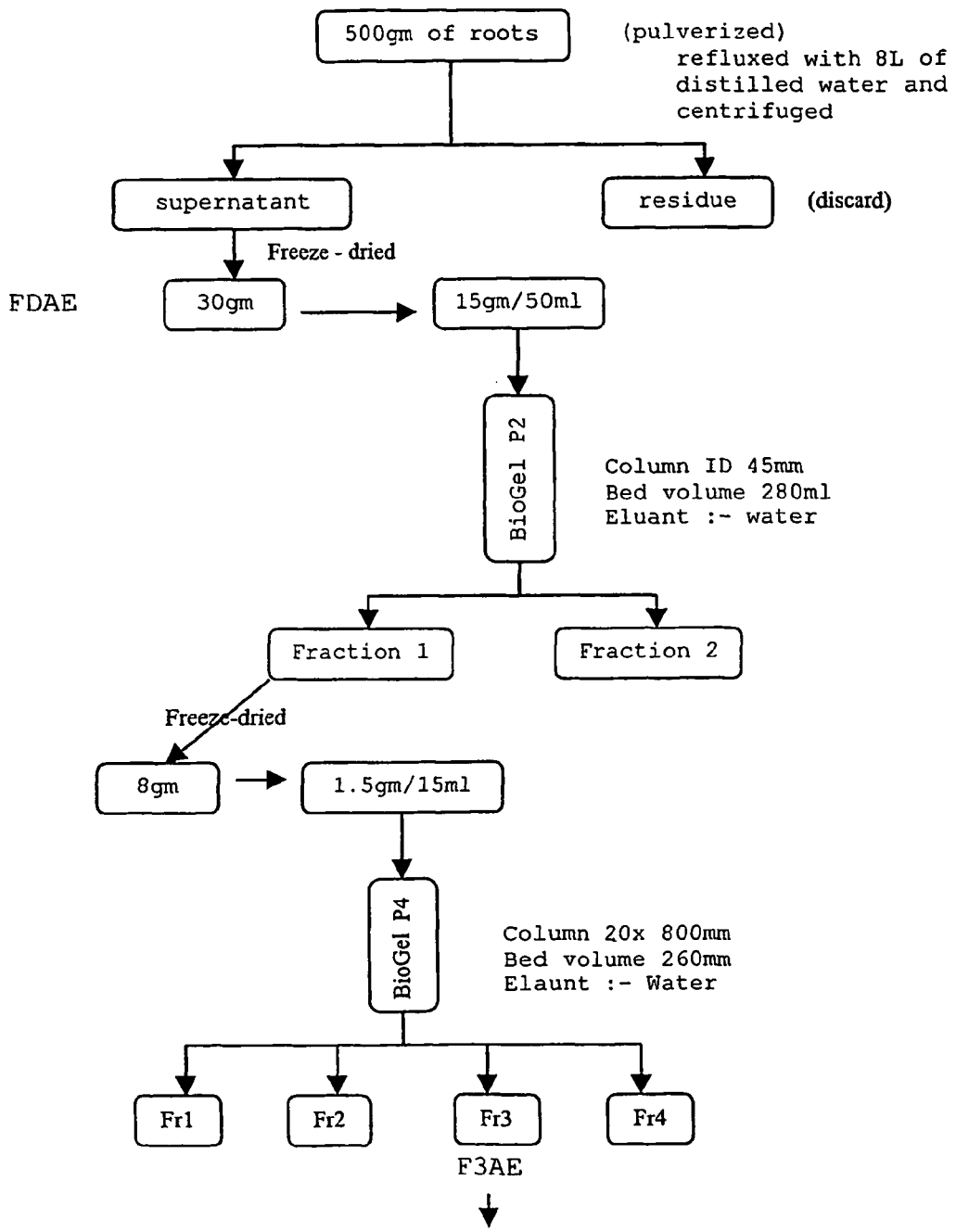
FIG. 1 shows a schematic flowchart of the size-exclusion chromatographic procedure for isolating the bioactive fraction of *Eurycoma longifolia*. Bioactive fractions FDAE and F3AE are recovered at the steps indicated.
Figure 2:
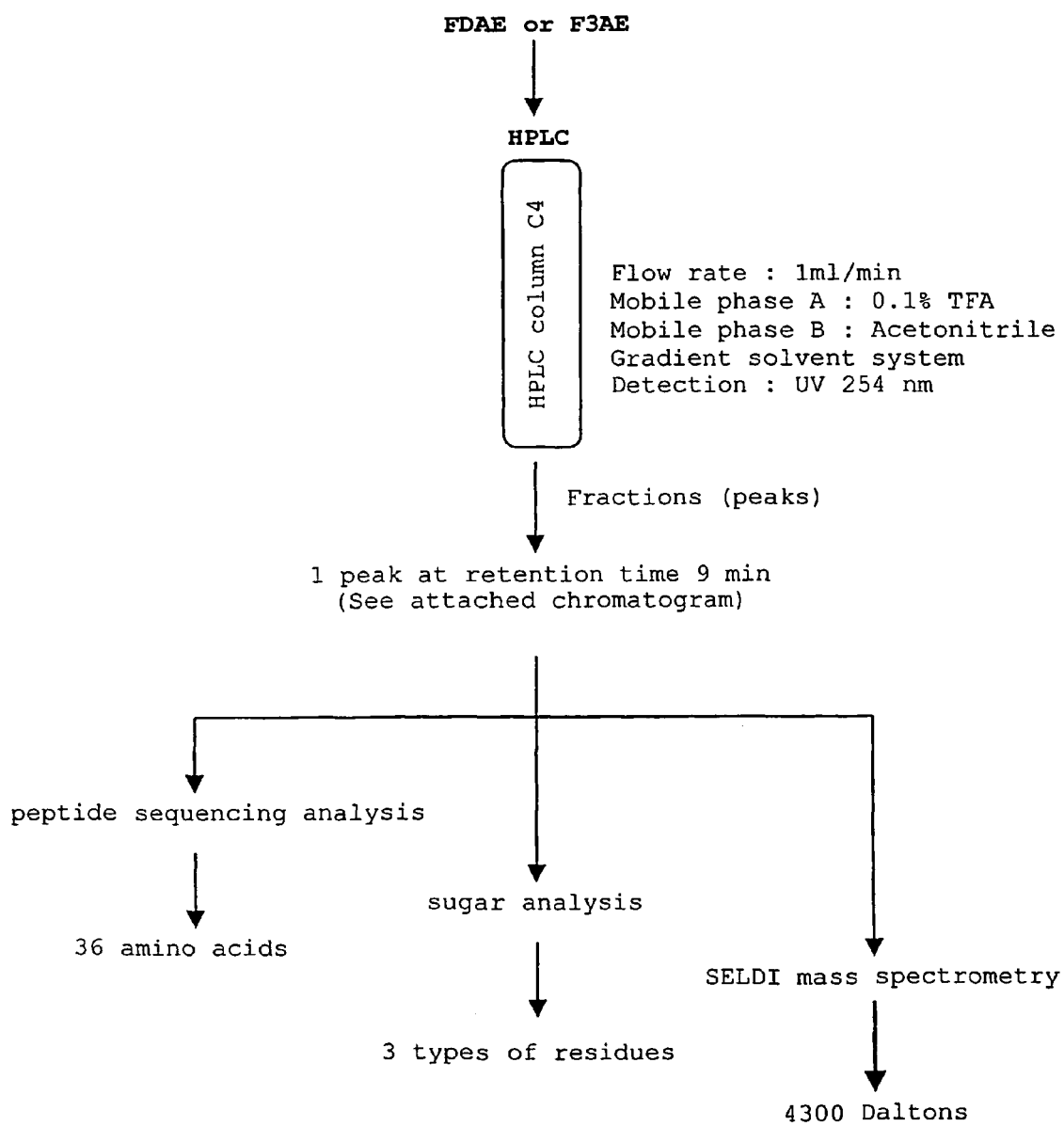
FIG. 2 shows a schematic flowchart of the reverse-phase HPLC purification for the bioactive fraction of *Eurycoma longifolia*.

The present invention is directed to the use of bioactive fractions of extracts of *Eurycoma longifolia* for use in treatment of male infertility and sexual dysfunction. Male infertility is a widespread problem and encompasses many aspects including but not limited to: abnormal libido, abnormal sperm motility, and abnormal sperm count. These types of abnormalities may be related to abnormally low testosterone levels. Male infertility is difficult to treat. For example, "two thirds of infertile men have a partial reduction in semen parameters and subfertility" and "a variety of empirical therapies (e.g. testosterone rebound, gonadotrophins, anti-estrogens) have been unsuccessful" (Harrison's Principles of Internal Medicine, 1998). In addition to infertility, reduced testosterone levels may be correlated to lack of sexual function and reduced libido that plague many aging, and in some cases young, men. The present invention is also directed to fertility and anti-sexual dysfunction preparations including such bioactive fractions.

The present invention includes the identification of the bioactive component of *Eurycoma longifolia* (for increasing testosterone release or production or sperm motility or number) as a peptide molecule, likely a glycopeptide. As shown in the Examples below, a peptide having a molecular weight of about 4300 daltons was purified by a series of chromatographic processes culminating in a reverse-phase high-performance liquid chromatography (HPLC) purification step. Analysis of the isolated and purified bioactive fraction indicated the presence of a bioactive peptide of about 4300 daltons associated with several types of sugar residues.

*Eurycoma longifolia* extracts as starting materials for the chromatographic processes described herein may be obtained by aqueous extraction of *Eurycoma longifolia*. In preferred embodiments, only the roots of the plant are used. In preferred embodiments the roots are pulverized. A variety of hydrophilic solvents can be used in the extraction procedure, including e.g., water, methanol, ethanol, and other lower alkyl alcohols. Pulverized roots may be boiled in a solvent and debris removed from the extract by centrifugation. Multiple extractions may be performed to further refine the aqueous extract.

As described herein, a variety of chromatographic procedures can be used to isolate fractions containing the active ingredient of *Eurycoma longifolia*. Such chromatographic processes include size-exclusion chromatography, gel-filtration chromatography, high-performance liquid chromatography (HPLC), reverse-phase HPLC, and ion-exchange chromatography. In one embodiment the chromatographic procedure may be size-exclusion chromatography. As would be understood by one skilled in the art, in some embodiments size-exclusion chromatography may be performed with polyacrylamide beads such as Bio-Gel P-2 or Bio-Gel P-4 and in other embodiments the size exclusion chromatography may be performed with other size-exclusion products from the same or other manufacturers. Methods of selecting size-exclusion materials and methods would be routine to those familiar with the chromatographic arts.

In other embodiments the chromatographic procedure may be reverse-phase HPLC. Preferably, in one embodiment the column comprises a silica based adsorbent. In some embodiments the reverse-phase HPLC column is a C4 (butyldimethylchlorosilane) column. In other embodiments the reverse-phase HPLC column is a C18 (octadecyl) column. As would be understood by one of ordinary skill in the art, also the column may be selected from among, but is not limited to: C8, C1 (trimethylchlorosilane), CN, or phenyl columns. Methods of selecting reverse-phase TPLC columns, adsorbents, and adsorbent modifications would be routine to those familiar with the chromatographic arts.

To assess the properties of *Eurycoma longifolia* extract fractions, a variety of experiments were performed using formulations of fractions. The details of these experiments are provided in the Examples below. Alternative methods to assay sperm motility, number, and testosterone levels are well known to those in the art, (e.g. see: Harrison's Principles of Internal Medicine, 1998; Winters et al., 1991; Froman and McLean, 1996; Bomman, et al, 1993) and would be understood to be usable in the assay of the bioactive fraction. In other embodiments, assessment of *Eurycoma longifolia* extract fractions may involve monitoring behavioral parameters as described herein.

In one set of embodiments, in addition to *Eurycoma longifolia* derived-compositions, e.g., fractions of *Eurycoma longifolia* extracts, the preparations of the present invention include a pharmaceutically acceptable carrier for oral administration.

In order to facilitate oral administration, *Eurycoma longifolia* derived compositions may be mixed with any of a variety of pharmaceutically acceptable carriers for oral administration. By the term "pharmaceutically acceptable carrier for oral administration" is meant a composition which is non-toxic, is not irritating to the human gastrointestinal system, and which can be mixed with *Eurycoma longifolia* derived compositions to form a solution, syrup, emulsion, gel, or solid. Preparations for intravenous, intramuscular, subcutaneous or, in general, parenteral administration may also be produced by methods known in the art.

Some example of substances which can serve as pharmaceutically acceptable carriers for oral administration are sugars such as lactose, glucose and sucrose; starches such as corn starch and potato starch; cellulose and its derivatives, such as sodium carboxymethycellulose, ethylcellulose, and cellulose acetate; powdered tragacanth; malt; gelatin; talc; stearic acid; magnesium stearate; calcium sulfate; vegetable oils such as peanut oil, cotton seed oil, sesame oil, olive oil, and corn oil; polyols such as propylene glycol, glycerine, sorbitol, mannitol, and polyethylene glycol; polyvinylpyrrolidone; alginic acid; pyrogen-free water; isotonic saline; phosphate buffer solutions; cocoa butter; emulsifiers; as well as other non-toxic compatible substances used in pharmaceutical formulations. Wetting agents and lubricants such as magnesium stearate, as well as coloring agents, flavoring agents, excipients, tableting agents, stabilizers, antioxidants, and preservatives, can also be present. Other compatible pharmaceutical additives and actives may be included in the pharmaceutically acceptable carrier for use in the compositions of the present invention.

The preparations for oral administration may be in the form of tablets, caplets, soft and hard gelatin capsules, pills, including delayed or prolonged release formulations, dispersible powders or granules, lozenges, sachets, cachets, elixirs, suspensions, emulsions, solutions, syrups, aerosols, (as a solid or in a liquid medium), and the like.

In other sets of embodiments, in addition to *Eurycoma longifolia*-derived-compositions, e.g., fractions of *Eurycoma longifolia* extracts, the preparations of the present invention include a pharmaceutically acceptable carrier for topical application. Such pharmaceutically acceptable carriers are well known in the art and, in essence, may include any currently used and commercially available dermatological or cosmetic preparation, or combinations of currently used and commercially available dermatological or cosmetic preparations. Thus, one may simply modify an available dermatological or cosmetic preparation by adding a *Eurycoma longifolia*-derived composition and adjusting, as necessary, the ratios of aqueous and non-aqueous components to maintain a consistency suitable for a topical application.

As used herein, the term "pharmaceutically acceptable carrier for topical application" means a composition suitable for topical application to human skin by spreading or rubbing, which does not cause irritation to human skin, and which can be mixed with *Eurycoma longifolia*-derived compositions to form a solution, emulsion, gel, lotion, ointment, balm, cream, or spreadable solid or paste. Such pharmaceutically acceptable carriers may include emollients, surfactants, humectants, lubricants, thickeners, waterproofing agents, bactericidal agents, percutaneous penetrating agents and preservatives. In addition, various cosmetic agents, such as fragrances and pigments may be included in a pharmaceutically acceptable carrier for topical application.

One embodiment where use of a composition for the treatment of sexual dysfunction or male infertility as described herein is the administration to a subject the bioactive agent derived from *Eurycoma longifolia*. As used herein, a subject is a human, non-human primate, cow, horse, pig, sheep, goat, dog, cat, or rodent. In all embodiments human subjects are preferred. In all embodiments male subjects are preferred. Preferably the subject is a human suspected of having sexual dysfunction or of being infertile or having been diagnosed with sexual dysfunction or infertility.

In one embodiment of the present invention, a method for increasing: testosterone synthesis, testosterone release from testis cells, sperm count, and/or sperm motility is disclosed which employs a preparation including a *Eurycoma longifolia*-derived composition that comprises the bioactive agent. In one embodiment, the preparation of *Eurycoma longifolia*-derived composition may be administered in conjunction with other medicaments known to those of skill in the art to increase: testosterone synthesis, testosterone release, sperm count, or sperm motility. For example, application of a slow-release testosterone patch may be accompanied with concurrent administration of the *Eurycoma longifolia* bioactive formulation.

The *Eurycoma longifolia* bioactive formulations of the invention are administered in effective amounts, alone or in a cocktail with other compounds. An effective amount is one sufficient to increase: testosterone synthesis, testosterone release from the testis, sperm count or sperm motility. Effective amounts will depend, of course, on the severity of the condition being treated; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is the highest safe dose according to sound medical judgement.

Generally, daily doses of active compounds will be from about 0.01 milligrams/kg per day to 2000 milligrams/kg per day. It is expected that oral doses in the range of 10 to 500 milligrams/kg, in one or several administrations per day, will yield the desired results. In the event that the response in a subject is insufficient at such doses, even higher doses (or effective higher doses by a different, more localized delivery route) may be employed to the extent that patient tolerance permits. Dose ranges can be adjusted as necessary for the treatment of individual patients and according to the specific condition treated. Multiple doses per day are contemplated to achieve appropriate systemic levels of compounds.

A variety of administration routes are available. The particular mode selected will depend of course, upon the particular formulation selected, the severity of the condition being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, transdermal or parenteral routes. The term "parenteral" includes subcutaneous, intravenous, intramuscular, or infusion. Intravenous and intramuscular routes are not particularly suited for long term therapy and prophylaxis. Intravenous administration is preferred in acute emergency situations. Oral administration will be preferred for prophylactic treatment because of the convenience to the patient as well as the dosing schedule.

The compositions may conveniently be presented in unit dosage form and may be prepared by any of the methods well known in the art of pharmacy. In general, the compositions are prepared by uniformly and intimately bringing the active compounds into association with a liquid carrier, a finely divided solid carrier, or both, and then, if necessary, shaping the product.

Compositions suitable for oral administration may be presented as discrete units such as capsules, cachets, tablets, or lozenges, each containing a predetermined amount of the active compound. Other compositions include suspensions in aqueous liquors or non-aqueous liquids such as a syrup, an elixir, or an emulsion.

Other delivery systems can include time release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di- and triglycerides; hydrogel release systems, silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775 (Kent); 4,667,014 (Nestor et al.); and 4,748,034 and 5,239,660 (Leonard) and (b) diffusional systems in which an active component permeates at a controlled rate through a polymer, found in U.S. Pat. Nos. 3,832,253 (Higuchi et al.) and 3,854,480 (Zaffaroni). In addition, a pump-based hardware delivery system can be used, some of which are adapted for implantation.

Example 1

Isolation of *Eurycoma longifolia* Bioactive Fractions

Introduction

Partially purified extracts of roots from *Eurycoma longifolia* were obtained through several purification steps including reflux and two rounds of size-exclusion chromatography.

Method

The initial step in the isolation of bioactive fraction of *Eurycoma longifolia* was the pulverization of 500 gm *E. longifolia* root followed by boiling 8hr in 8 L distilled water. The boiled mixture was then centrifuged, the pellet discarded, and the clarified supernatant collected and freeze dried yielding approximately 30gm. This fraction was identified as "FDAE" and a portion of the FDAE was set aside for additional purification and assay in Examples 3 and 4. From the remaining freeze-dried FDAE pellet, 15gm was resuspended in 50 ml distilled water and loaded onto a Bio-Gel P-2 column (Bio-Rad Laboratories, Hercules, Calif.) with 45-mm internal diameter and 280-ml bed volume, and eluted from the column with distilled water. The eluate was collected in two fractions, which were distinguished by color with the initial fraction brown in color and second fraction fluorescent yellow in color. The initial fraction (fraction one) was freeze dried.

From the freeze-dried fraction 1.5 gm was resuspended in 10–15 ml distilled water and loaded onto a 20×800mm, 260ml bed volume Bio-Gel P-4 column (Bio-Rad Laboratories, Hercules, Calif.) and eluted off with distilled water. Based on distinguishing coloration, four fractions of the eluate were collected and freeze dried and used to measure bioactivity. FIG. 1 summarizes the purification scheme.

Results

The third eluted fraction was identified as "F3AE". A portion of F3AE was utilized in bioactivity experiments as described in Example 2 and a portion of F3AE was further purified as described in Example 3.

Example 2

Bioassay of Bioactive Fractions from *Eurycoma longifolia* Purification Procedures

Introduction

To assess the bioactivity of the third eluted fraction F3AE a portion of the eluted fraction was assayed using standard testosterone and sperm assessment methods.

Method

Using standard procedures, in vitro radioimmunoassay measurements of testosterone were made using plasma from test and control animals. In addition, in vitro hormone assays were performed using standard gas chromatographic methods. Sperm analysis for concentration and motility were performed using standard methods.

Results

The results of the bioassays are given in Table 1.

TABLE 1

Results of in vivo and in vitro assays of bioactivity

| Assay | | Sample | Control |
|---|---|---|---|
| In vivo hormone assays - HA | | 114.6 pg/ml | 67.6 pg/ml |
| In vitro hormone assay - GC | | 2.4 µg | 0.9 µg |
| Sperm analysis | - concentration | 99 Mil/ml | 74 Mil/ml |
| | - progressive sperm | 39% | 22% |
| | - motility rate | 71% | 64% |

Example 3

Alternative Method for Isolation of Bioactive Fractions of *Eurycoma longifolia*

Introduction

Following the initial separation of the fractions from *Eurycoma longifolia* (see Example 1). A portion of FDAE (See Example 1) and a portion of the bioactive fraction F3AE isolated from the *E. longifolia* root (see Example 2) was purified using reverse-phase HPLC methods and characterized using amino acid analysis, sugar analysis, and mass spectroscopy methods.

Method

Either fraction FDAE or fraction F3AE (see Example 1 and 2 Methods sections) was loaded onto a Rainin C4 column on a Rainin HPLC system (Rainin Instrument Co., Woburn, Mass.) for reverse-phase separation. The 60 minute BPLC purification was run utilizing a constant 1 ml/min flow rate. Either FDAE or F3AE at about 1 mg/ml distilled water, was injected at time 0. The mobile phase was 100% 0.1% trifluoroacetic acid (TFA) for the first 10 minutes and was then transitioned from 100% 0.1% TFA to 100% acetonitrile over the remaining 50 minutes of the run. Fractions were collected throughout the run and the eluate was monitored with 245-nm UV detection, and subsequently freeze dried. FIG. 3 provides chromatographic traces from the separations with A from the FDAE run and B from the F3AE run. A single peak indicated by the "*" in lower trace in FIG.

3 represents the bioactive fraction characterized in Example 2. The content of the single peak eluted at nine minutes was subjected to peptide analysis and sugar analysis using standard methods. Mass spectroscopy analysis was also performed on the nine-minute fraction as per manufacturer's instructions using surface enhanced laser desorption ionization (SELDI; e.g., Ciphergen, Palo Alto, Calif.).

Results

The single peak elution at nine minutes was determined to be bioactive based on the bioassays described in Example 2. The peak was analyzed by several methods to determine its composition. The compound eluted at nine minutes was determined to consist of about 33–36 peptides; to be associated with about three types of sugars including xylose, glucoses and fucose; and to have a mass of about 4300 daltons.

REFERENCES

Chan K. L., C. Y. Choo, H. Morita, and H. Itokawa, (1998) High performance Liquid Chromatography in Phytochemical Analysis of *Eurycoma longifolia*. Planta Medica 64:741–745.

Harrison's Principles of Internal Medicine, 14/e, (1998) McGraw-Hill Companies, New York.

Winter., S. J., R. Medhamurthy, V. L. Gay, and T. M. Plant (1991) A comparison of moment to moment and diurnal changes in circulating inhibin and testosterone concentrations in male rhesus monkeys (*Macaca mulatta*). *Endocrinology* 129(4):1755–61.

Froman, D. P. and D. J. McLean (1996) Objective measurement of sperm motility based upon sperm penetration of Accudenz. *Poult. Sci.* 75(6):776–84.

Du Toit, D., M. S. Bornman, M. P. Van DerMenve, D. J. Du Plessis, and J. M. Oosthuizen (1993) Differential sperm motility scoring and sperm ATP concentrations. *Arch. Androl.* 30(1):69–71.

Although the invention has been described above with respect to various presently preferred embodiments, it will be apparent to one of ordinary skill in the art that many variations and modifications may be made. Therefore, the invention is not to be understood as limited to the particular embodiments recited herein but, rather, is to be understood as embracing all such variations and modifications which fall within the spirit and scope of the claims appended hereto.

All references disclosed herein are incorporated by reference in their entirety.

The invention claimed is:

1. A composition for treating male sexual dysfunction, treating male infertility, increasing testosterone synthesis, increasing testosterone release from testis cells, increasing sperm count, or increasing sperm motility in a subject comprising an effective amount of a fraction of an aqueous extract of *Eurycoma longifolia*, wherein the fraction comprises a peptide having a molecular weight of about 4300 daltons.

2. The composition of claim 1, wherein the fraction has an activity selected from the group consisting of increasing testosterone synthesis, increasing testosterone release from cells, increasing sperm count, and increasing sperm motility.

3. The composition of claim 1, wherein the peptide is a glycopeptide.

4. The composition of claim 1, wherein the peptide has about 30–39 amino acids.

5. The composition of claim 4, wherein the peptide has about 36 amino acids.

6. A method for the treatment of sexual dysfunction or male infertility comprising administering to a subject in need of such treatment an amount of the composition of claim 1 effective to increase an activity selected from the group consisting of increasing testosterone synthesis, increasing testosterone release from cells, increasing sperm count and increasing sperm motility.

7. A method for increasing testosterone synthesis comprising administering to a subject in need of such treatment an amount of the composition of claim 1 effective to increase testosterone synthesis.

8. A method for increasing testosterone release from testis cells comprising administering to a subject in need of such treatment an amount of the composition of claim 1 effective to increase testosterone release from testis cells.

9. A method for increasing sperm count comprising administering to a subject in need of such treatment an amount of the composition of claim 1 effective to increase sperm count.

10. A method for increasing sperm motility comprising administering to a subject in need of such treatment an amount of the composition of claim 1 effective to increase sperm motility.

11. A pharmaceutical composition comprising an effective amount of the composition of claim 1 and a pharmaceutically acceptable carrier.

12. A method for isolating a bioactive component from an aqueous extract of *Eurycoma longifolia*, comprising
preparing an aqueous extract of *Eurycoma longiolia*, and
isolating the bioactive component by a chromatographic method selected from the group consisting of reverse-phase high performance liquid chromatography (HPLC) and size-exclusion chromatography, wherein the bioactive component comprises a peptide having a molecular weight of about 4300 daltons.

13. The method of claim 12, wherein the reverse-phase HPLC is performed using a chromatographic medium selected from the group consisting of C4 and C18.

14. The method of claim 12, further comprising fractionating the aqueous extract using at least one size-exclusion chromatography medium selected from the group consisting of Bio-Gel P-2 and Bio-Gel P-4 prior to separation by chromatography by reversed phase HPLC.

15. The method of claim 12, wherein the bioactivity is selected from the group consisting of increasing testosterone synthesis, increasing testosterone release from cells, increasing sperm count and increasing sperm motility.

16. A bioactive component of *Eurycoma longiolia* prepared by the method of claim 12.

* * * * *